United States Patent [19]

Abu-Shumays

[11] 4,262,205
[45] Apr. 14, 1981

[54] FLUOROMETER WITH HIGH SENSITIVITY AND STABILITY

[75] Inventor: Ahmad Abu-Shumays, Los Altos, Calif.

[73] Assignee: Varian Associates, Inc., Palo Alto, Calif.

[21] Appl. No.: 77,817

[22] Filed: Sep. 21, 1979

[51] Int. Cl.³ .............................. G01J 1/58; G01J 3/30
[52] U.S. Cl. ................................... 250/458; 356/318; 250/461 B
[58] Field of Search ................... 250/458, 459, 461 R, 250/461 B; 356/318, 323, 324, 417

[56] References Cited

U.S. PATENT DOCUMENTS

| | | | |
|---|---|---|---|
| 3,497,690 | 2/1970 | Wheeless, Jr. et al. | 250/461 B |
| 3,832,555 | 8/1974 | Ohnishi | 250/458 |
| 3,886,363 | 5/1975 | Ohnishi et al. | 250/364 |
| 3,897,155 | 7/1975 | Smythe | 356/85 |
| 3,999,062 | 12/1976 | Demsky et al. | 250/227 |
| 4,180,739 | 12/1979 | Abu-Shumays | 250/461 |

OTHER PUBLICATIONS

Morgenthaler et al., "Application of a Microcomputer System for Control of an Atomic Absorption Spectrometer", Aug. 1976, American Laboratory, pp. 37–45.

*Primary Examiner*—Davis L. Willis
*Assistant Examiner*—Janice A. Howell
*Attorney, Agent, or Firm*—Stanley Z. Cole; Gerald M. Fisher

[57] ABSTRACT

The present inventive fluorometer provides a rapid means for accurate sample quantitative measurements by making instrumental calibration measurements during sample equilibration time. Increased speed of equilibration and calibration and simultaneously performing these two functions increases the throughput speed with which individual measurements can be accomplished, thus increasing the number of samples which can be routinely processed. This decreases the cost per test and more importantly renders new treatment protocols possible which require the doctor and patient to be able to know within minutes the level of certain drugs in various body fluids.

6 Claims, 4 Drawing Figures

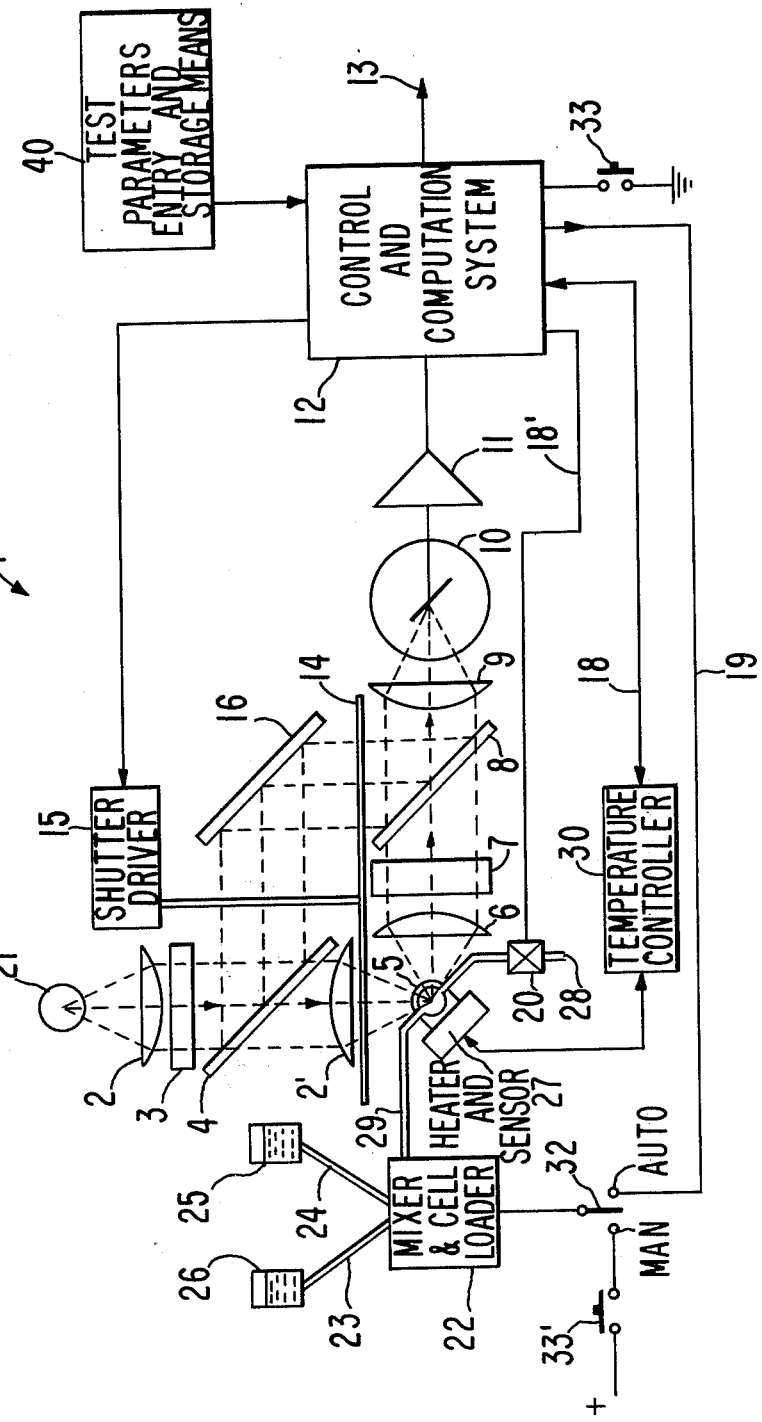

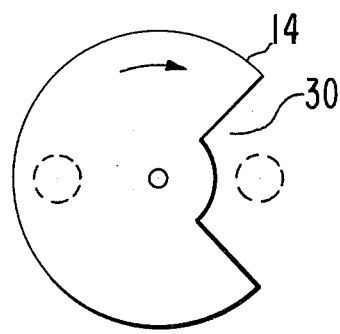
FIG.2A
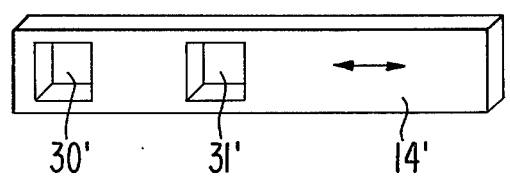
FIG.2B
FIG.3
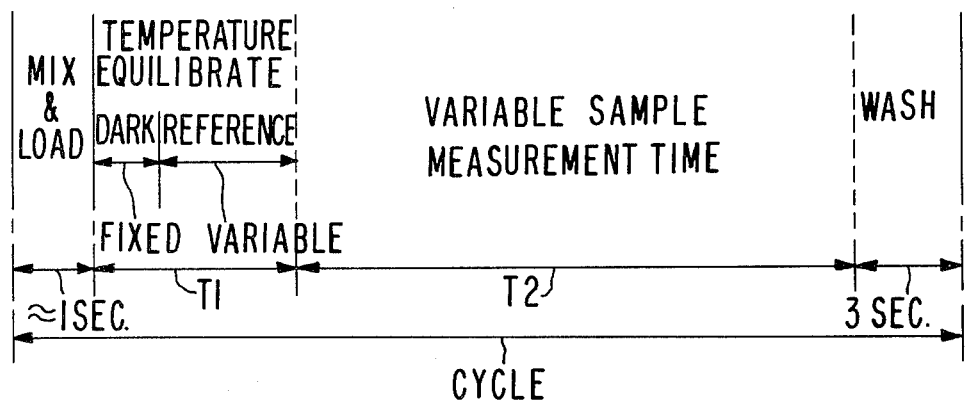

FLUOROMETER WITH HIGH SENSITIVITY AND STABILITY

FIELD OF THE INVENTION

This invention relates to fluorometer systems for rapidly equilibrating the temperature of a sample and for measuring its fluorescence. More particularly, the invention is directed to methods and apparatus providing highly stable and highly sensitive fluorometry measurements.

DESCRIPTION OF THE PRIOR ART

Prior art fluorometers are known employing both single beam or double beam optical paths. When using a single beam instrument, to calibrate the instrument for instrumental drifts and offsets, it is customary to place a sample material having a known response into the beam. This is frequently done prior to and after taking a measurement with an unknown material. While single beam instruments exhibit high sensitivity due to their high optical throughput, they suffer from drift and gain instability. Factors influencing the stability include characteristics of the light source, the photodetector, and the measuring system. It is not uncommon for such systems to exhibit 10 percent (10%) variations in the output signal for the same "known" sample during the course of a few hours. Therefore, it is necessary when using such single beam systems to perform very frequent "calibrations" of the instrument using standard samples to assure accurate quantitative measurements. Clinical application would require calibration at the time of each measurement.

In double beam instruments, a fraction of the exciting radiation is channeled through a separate optical path to provide a reference signal while the bulk of the exciting radiation impinges upon the sample providing a sample signal. Double beam, dual detector systems typically automatically compensate their measurements for variations in the light intensity from the lamp, but since two detectors have dissimilar characteristics, double beam, dual detector instruments exhibit a residual uncompensated drift of several percent during the course of a few hours. Another uncompensated factor in such double beam, dual detector systems results from optical/physical changes in the reference and sample channels relative to one another.

Double beam, single detector fluorometers overcome the problems of detector mismatch and in general provide excellent compensation for drift and gain instability. In double beam systems, either single or dual detector, a chopper is typically used to sequentially select the photodetector dark current, the reference channel or the sample channel to be observed. Typically a chopper is rotated at high constant angular speeds, about 1800 rpm, and the chopper position is monitored to signal sample, reference, and dark measurements intervals. This information is transmitted to three corresponding digitizers or sample and hold networks in order to derive a corrected signal in a well-known manner. Higher speed chopper operation improves stability by providing more frequent calibration measurements.

Variations in lamp intensity, detector response and drift of measurement electronics are correctable in these double beam chopper schemes since these variations contribute equally to expressions in both the numerator and denominator of an expression of the form of $S^* = (S-D)/(R-D)$ where $S^*$ = corrected signal
$S$ = measured sample signal
$R$ = measured reference signal
$D$ = measured dark signal Hence, double beam fluorometers provide considerably better stability and compensation than single beam fluorometers. However, we have determined that the double beam-constant speed chopper approach has disadvantages for measurement of rapidly completing fluorescent reactions. A double beam fluorometer cycle is typically divided equally between sample, reference, and dark interval measurements. Thus, the actual sample time/unit time spent on monitoring the sample is reduced by two-thirds from the single beam configuration which monitors the sample signal continuously. This time sharing situation in double beam systems results in a corresponding loss in sensitivity for dynamic reaction measurements for samples in which the fluorescence intensity is changing as a function of time. The measurement precision becomes increasingly inferior for fast reactions. This is particularly true for observation of small sample quantities where emission intensity is very low and where the instrument stability is critical. The inventive fluorometry system provides a double beam, single detector configuration wherein the chopper or shutter is stationary in the sample measurement position during a long period of time so that the instrument is configured as a single beam instrument during sample measurement and where the instrument calibration measurements using the other channel (reference) are made during the period of sample temperature equilibration immediately prior to measurement.

The object of the present invention is to provide a fluorometer system which exhibits an extremely high degree of stability as well as very high signal sensitivity.

It is a further object of this invention to provide a fluorometer system which can accurately measure fluorescence as a function of time on fast reactions or small sample quantities wherein reference and dark current measurements are automatically made, after a cycle has started, during the same time that rapid thermal equilibration of the sample is accomplished and where the sample fluorescence signal monitoring, once started, can be monitored continuously without interruption until stopped. Another object of the present invention is to provide the equivalent of the electronic compensation available in a double beam system and the sensitivity of a single beam system.

BRIEF DESCRIPTION OF THE DRAWINGS

The invention is diagrammatically illustrated, by way of example, in the drawings appended hereto, in which:

FIG. 1 is a simplified block diagram setting forth the basic elements of the inventive fluorometer system;

FIGS. 2A and 2B illustrate alternative configurations of a shutter or chopper;

FIG. 3 illustrates a typical timing cycle employing the subject invention.

DESCRIPTION OF THE PREFERRED EMBODIMENT

In FIG. 1 herein a simplified block diagram appears setting forth the key elements forming part of the present fluorometer. In system 1, excitation light emitted by an appropriate source lamp 21 is collimated using lens 2 and is filtered to select an appropriate wavelength band using filter 3. The output of filter 3 forms an exciting beam which is split into reference and sample channel beams by beam splitter 4. During sample measurement the portion of the light beam directed into the sample channel through shutter 14 is focused via lens 2' on sample cell 5. The sample cell 5 is a tiny fluorescence flow cell enabling rapid temperature equilibration which cell is described in copending application, Ser. No. 864,137, filed Dec. 23, 1977, by the same inventor now U.S. Pat. No. 4,180,739.

Light emitted by the fluorescing sample in cell 5 is collimated by lens 6 and passes through filter 7 for focusing onto semitransparent mirror 8. Light passes through the semitransparent mirror 8 and is then focused by lens 9 on photodetector 10.

The light signal detected by photodetector 10 is input to amplifier 11, the output of which is passed to control and computation system 12 for processing. The corrected output for each measurement is then provided at output means 13.

Test parameters which are input to the test parameter entry and storage means 40 are provided to the control and computation system 12, which control the times for T1 and T2 period (FIG. 3) for a particular designated type of measurement. For rate measurements in quickly saturating reactions, T1, the time to temperature equilibrate the sample, is as short as possible, i.e., 5 sec. For reactions in which the stabilized fluorescence intensity level is to be measured, T1 may be set to end and T2 commence when the fluorescence or reaction rate of the mixture is expected to be stabilized. The test parameter entry and storage means 40 can be a keyboard, an optical card reader, a magnetic card reader or any other appropriate means for inputing the test parameters to the control and computation system 12.

When a sample is loaded into cell 5, for system calibration, shutter 14 is positioned by shutter indexing driver 15 such that the excitation beam is blocked so that it does not fall onto semitransparent mirror 8 or onto the sample cell. This permits a calibration of the photocell 10 output current when no light is incident thereto. This current is called the "dark current." The shutter 14 is disclosed in FIG. 2A with appropriate aperture 30 which can be adjusted to simultaneously pass one path and block the other path as well as block both paths simultaneously. Alternately the configuration of FIG. 2B could also be employed as a shutter or mask to effect the same result.

Reference channel measurements for calibration purposes are also made during the same time that the temperature of the sample is being equilibrated. The shutter driver 15 is commanded by the control and computation system 12 so that the portion of the excitation beam directed into the reference channel by the beam splitter 4 falls onto mirror 16 and is directed towards semitransparent mirror 8. Shutter 14 is positioned to permit this light to pass to mirror 8. The light beam striking semitransparent mirror 8 is deflected to lens 9 and focused onto photodetector 10. This signal is amplified and processed to provide an electronics drift calibration signal. The reference channel calibration preferably continues up to the instant that sample measurements are started. Preferably the dark current measurement is a fixed time interval, and the remainder of the T1 interval is determined by the control 12 in response to test parameter input information.

Control and computation system 12 commands the shutter 14 positioning such that the sample measurement period starts at the correct time and is long enough for the signal-to-noise ratio to be high even though the reaction to be measured is very quick, i.e., completed in 20 seconds. For low level signals or for rapidly changing signals the sample measurement time is long in comparison to the time during which source lamp and dark current measurements are performed. This provides for uninterrupted integration of the signal and hence maximum signal-to-noise ratio capabilities.

Mixer and cell loader 22 controls the introduction of sample fluid into the sample cell 5 through conduit 29. In auto position of switch 32, upon initiation of start switch 33, a control signal from control 12 on line 19 causes a measured amount of sample fluid from the sample reservoir 26 and reagent from the reservoir 25 to mix together and to be introduced into the cell 5. Alternately, mixing and loading can be manually carried out with switch 32 in manual, or the mixer and loader can be initiated when switch 32 is in manual position by closing switch 33'. Mixing can also be accomplished in the cell. Control 12 also initiates a signal on line 18' to activate and close valve 20 in the drain line 28 from sample cell in order to retain fluids in the cell during the equilibration and measurement periods. In auto position of switch 32, after initiation of switch 33, the start commands 18 and 18', respectively, are synchronized closely to the loading of mixed fluids of the cell 5 so that the calibration and correction measurements can take place immediately prior to sample measurement during the period that the sample is being brought to proper temperature, i.e., approximately 5 seconds.

This system provides an optimum time utilization because drifts present in the electronics and optics just at the instant of the start of measurement are recorded for compensation and correction of the immediately following measurement. With this system, the maximum sensitivity is possible because no interruption of the data takes place during measurement on the sample, especially during the critical early seconds in a measurement of quick reaction fluorescent experiments. Temperature controller 30 is connected to a thermoelectric device and to a thermocouple in heater and sensor 27 for rapid temperature equilibration at a selectable temperature.

With reference to FIG. 3, the preferred timing relationship for a typical experiment using the present inventive fluorometer is described. The length of the measurement period during which the sample is observed is selected by the test parameters entry and storage means 40 to start at the correct time in the reaction of the reagents employed and to be long enough to maximize the signal-to-noise ratio for the selected experiment. Use of a comparatively long period of time for the integration of the sample measurement provides sensitivity to sample concentrations in the picogram ($10^{-12}$ gm) per milliliter range. The configuration of the system during sample monitoring corresponds to equivalent arrangements employed by single beam fluorometers which afford five to ten fold improvement in detection limits relative to chopped double beam systems.

The inventive fluorometer system whereby the reference and dark current measurements are made during rapid temperature equilibration of the sample enables a study of a variety of sample types which could not be accurately handled with prior fluorometer systems. These include:

(1) Small sample quantities where the signal-to-noise ratio is very low. In the present system, measurement of the reference beam just prior to the sample measurement compensates for drifts in the instrument, without interrupting the integration during sample measuring period.

(2) Fast reaction rate experiments where the important measurement time window is short and which commence as soon as chemicals are brought together in the sample cell. This system provides the rapid temperature equilibration of the sample which permits measurement before the reaction has completed and which at the same time accomplishes the calibration measurements so that as soon as the sample reaches the specified temperature, sample measurements can commence uninterrupted by the need to calibrate.

(3) Large numbers of samples. This device has a high throughput measurement capability matching the clinical need which requires fast turn around time for large numbers of samples. The present inventive fluorometer provides a rapid means for accurate sample quantitative measurements by making instrumental calibration measurements during sample equilibration time. Increased speed of equilibration and calibration and simultaneously performing these two functions increases the throughput speed with which individual measurements can be accomplished, thus increasing the number of samples which can be routinely processed. This decreases the cost per test and more importantly renders new treatment protocols possible which require the doctor and patient to be able to know within minutes the level of certain drugs in various body fluids.

I claim:

1. A method for using a double beam instrument for obtaining highly stable fluorescence measurements of rapidly completing reactions comprising:

mixing a liquid sample to be studied with a reagent to form a mixture and rapidly adjusting and maintaining the temperature of said mixture to a selected equilibration temperature to enable calibrated fluorescence intensity measurements;

automatically performing, during the period of time immediately prior to achieving said selected temperature equilibration, measurements of instrumental error effects by sequentially placing a shutter means in second and third positions and measuring photocell output in said positions;

placing said shutter means in a first position;

and exciting said mixture with radiation to stimulate fluorescence while measuring and storing the intensity of emissions of said mixture, said measuring and storing being uninterruptedly carried out for a variable time determined by parameters of a particular test to be performed; and correcting said measured emission intensity for said instrument drifts in order to provide repeatable results.

2. A system for fluorescence measurements on rapidly completing reactions comprising:

a light source;
a photodetector;
a sample cell;
means for directing a portion of light from said light source in an excitation beam towards said cell in a first path and towards said photodetector in a second path;
means for collecting fluorescent emission from said cell along a path having a central axis 90 degrees displaced from said first path and directing said emissions to said photodetector;
a control and computation means being responsive to photodetector measurements and to test parameter input information;
means for rapidly controlling and achieving a selected temperature of said mixture in said cell, said means for rapidly controlling temperature being responsive to initiation from said control and computation means; and
shutter means, said shutter means having a first position for passing a portion of said excitation beam through said first path while precluding passage of any portion of said excitation beam through said second path and a second position for passing a portion of said excitation beam through said second path while precluding passage of a portion of said excitation beam through said first path, said shutter means also having a third position blocking passage of said excitation beam through both said paths, said shutter means being responsive to commands from said control and computation means for changing from position to position, in operation, said shutter means being positioned in said first position for a time controlled by said control and computation means based on the test parameters for the particular test and reagents being mixed with the sample.

3. A fluorometer of claim 2 wherein said means for rapidly controlling and achieving a selected temperature includes a tiny cell having a conductive wall intimately connected to a thermoelectric element and to a thermocouple element.

4. The fluorometer of claim 2 wherein, in operation, said shutter means is stationary during said sample measurement period in said first position.

5. An automated fluorescence measuring system comprising:

a control and computer means, said control and computer means for controlling the sequence of operation of said automated fluorescence measuring system and for correcting photometric data for instrumental drifts within said automated measuring system;
a fluorometer including a plurality of selectable beam paths for providing representations of reference signal, photodetector noise, and sample signal respectively, said beam path being selected responsive to said control and computer means;
means for providing test parameters for selected reagents to said control and computer means;
said control and computer means connected to said fluorometer to cause said fluorometer to perform calibration measurements of said instrument drifts during a first period, said first period being a temperature equilibration period for the sample to be tested which first period immediately precedes the selection of the beam path of said fluorometer for measuring the sample signal, said control and computer means responsive to said means for providing test parameters to control the duration during which the fluorometer is maintained uninterruptedly in the configuration of said beam path for providing a representation of said sample signal.

6. The automated fluorescence measuring system of claim 5 includes a sample cell, sample handling apparatus for controlling the washing, mixing of reagents, and loading of said sample cell responsive to said control and computer means, wherein said duration during which the fluorometer is maintained uninterruptedly in the configuration of said beam path for providing a representation of said sample signal is also a function of the time duration of the mixing of reagents and loading time of said cell.

* * * * *